Figure 4:
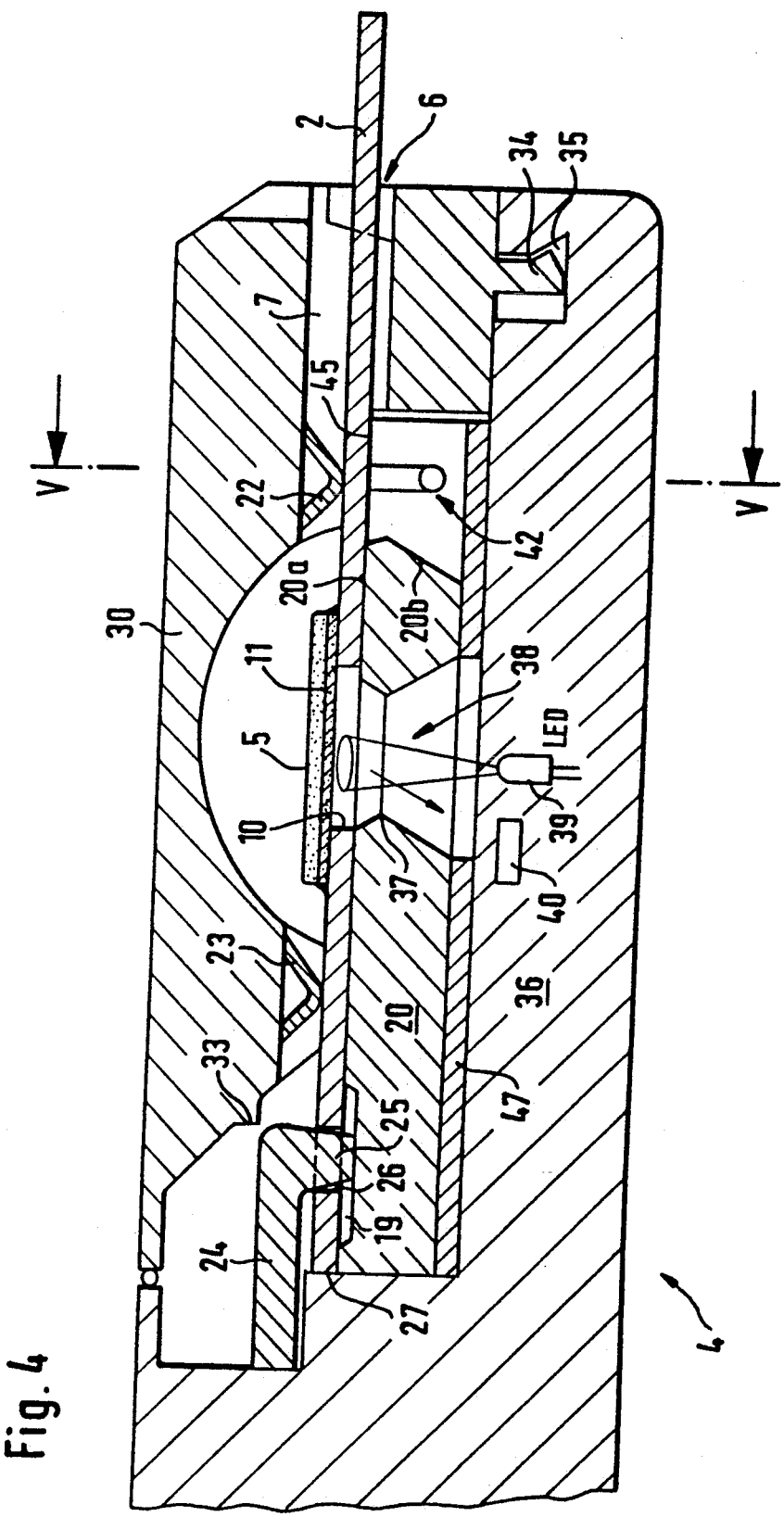

United States Patent [19]
Markart et al.

[11] Patent Number: 5,281,395
[45] Date of Patent: Jan. 25, 1994

[54] TEST CARRIER ANALYSIS SYSTEM

[75] Inventors: Ernst Markart, Munich; Franz Bolduan, Mannheim; Jörg Schreiber, Heddesheim, all of Fed. Rep. of Germany

[73] Assignee: Boehringer Manheim GmbH, Mannheim, Fed. Rep. of Germany

[21] Appl. No.: 808,808

[22] Filed: Dec. 18, 1991

[30] Foreign Application Priority Data

Dec. 27, 1990 [DE] Fed. Rep. of Germany ....... 4041905

[51] Int. Cl.⁵ ................. G01N 21/78; G01N 33/483; G06F 1/12; G06K 7/10
[52] U.S. Cl. ................. 422/82.05; 235/375; 235/462; 356/39; 356/243; 422/57; 422/58; 422/67; 422/68.1; 436/46; 436/48
[58] Field of Search ............ 422/56, 57, 58, 63, 422/67, 68.1, 82.01, 82.02, 82.05; 436/44, 46, 95, 47, 48, 524; 235/462, 375; 356/446, 36, 39, 243, 402

[56] References Cited

U.S. PATENT DOCUMENTS

| | | |
|---|---|---|
| 4,476,149 | 10/1984 | Poppe et al. . |
| 4,509,859 | 4/1985 | Markart et al. ............... 356/446 |
| 4,510,383 | 4/1985 | Rappender ................... 235/462 |
| 4,538,059 | 8/1985 | Rudland ........................ 235/468 |
| 4,592,893 | 6/1986 | Poppe et al. .................. 422/56 |
| 4,638,170 | 1/1987 | Kubota ........................... 250/566 |
| 4,780,283 | 10/1988 | Meinecke et al. ............ 422/68 |
| 4,871,258 | 10/1989 | Herpichboehm et al. ..... 356/422 |
| 4,985,205 | 1/1991 | Fritsche et al. ............... 422/56 |
| 5,035,862 | 7/1991 | Dietzer et al. ............... 422/68.1 |
| 5,037,614 | 8/1991 | Makita et al. ................ 422/68.1 |
| 5,053,199 | 10/1991 | Keiser et al. ................. 422/68.1 |
| 5,091,154 | 2/1992 | Pauli et al. .................. 422/63 |
| 5,122,645 | 6/1992 | Saeki et al. .................. 235/462 |
| 5,122,969 | 6/1992 | Seshimoto et al. ............ 364/497 |

FOREIGN PATENT DOCUMENTS

| | | |
|---|---|---|
| 0317325A3 | 5/1989 | European Pat. Off. . |
| 0353589A2 | 2/1990 | European Pat. Off. . |
| 0383322A2 | 8/1990 | European Pat. Off. . |
| 0405091A1 | 1/1991 | European Pat. Off. . |
| 2096314A | 10/1982 | United Kingdom . |

OTHER PUBLICATIONS

Accu-Chek®IIm, Blood Glucose Monitor Operator's Manual.

*Primary Examiner*—James C. Housel
*Assistant Examiner*—Milton I. Cano
*Attorney, Agent, or Firm*—Nikaido, Marmelstein, Murray & Oram

[57] ABSTRACT

Test carrier analysis system for analyzing a constituent of a body fluid, consisting of test carriers (2), code carriers (3) and an evaluation device (4). The test layers (5) of the test carrier (2) contain reagents whose reaction with the sample leads to a color change characteristic of the analysis in a detection layer. The code carriers (3) contain in machine-readable form an evaluation code with an evaluation curve required for the evaluation of the test carriers. The evaluation device (4) comprises a measuring device, a code reading device and evaluation electronics. Possible operating errors are eliminated, almost without additional expenditure, by the fact that single code reader containing two reading units offset relative to one another both laterally and in the reading direction is positioned on a common insertion path (28) both for the test carriers (2) and for the code carriers (3), the test carriers (2) possess a batch-specific identification code in the form of continuous strips, the evaluation code on the code carriers (3) is a two-track code and contains a batch identification, and the evaluation device (4) comprises a comparison unit for checking the correlation of the batch of the respective test carrier (2) to be evaluated with the stored evaluation information.

7 Claims, 3 Drawing Sheets

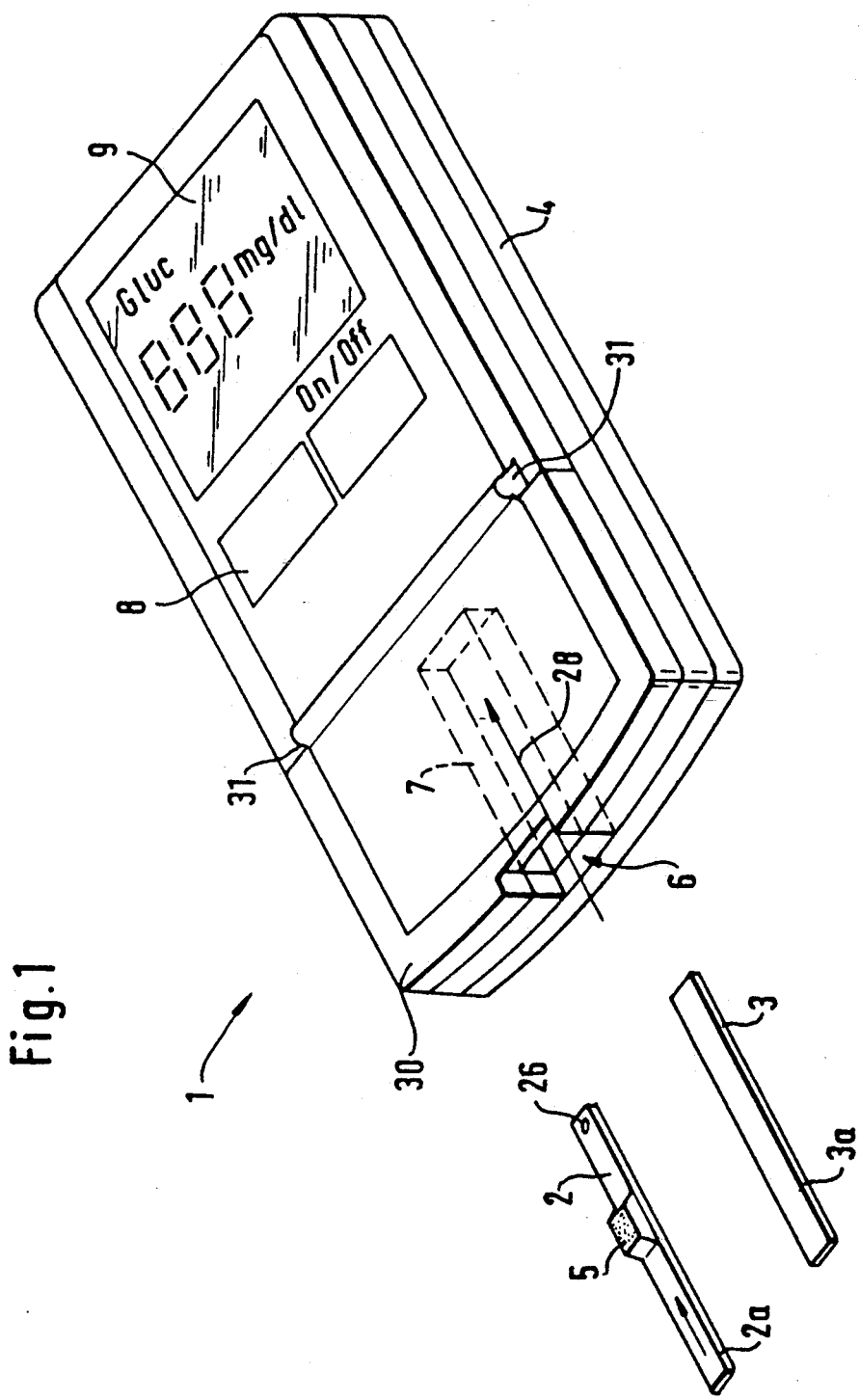

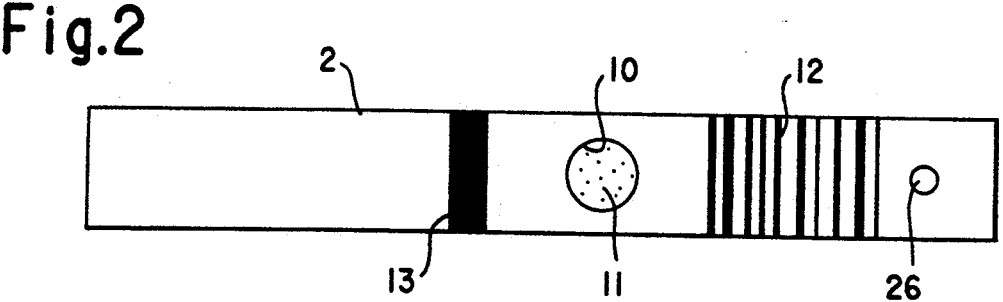
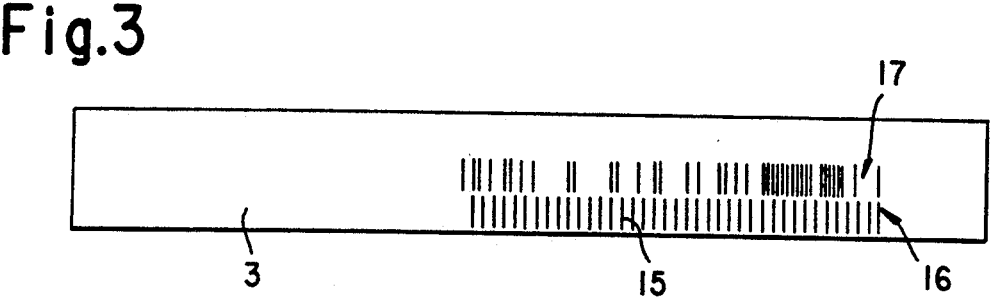
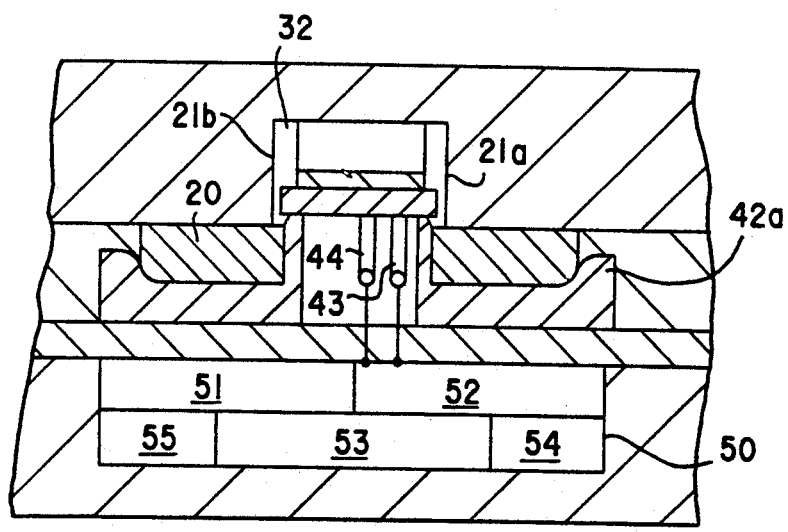
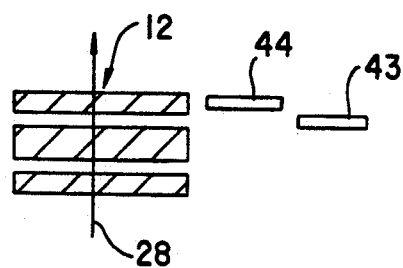

TEST CARRIER ANALYSIS SYSTEM

The invention relates to a test carrier analysis system for analyzing a constituent of a fluid sample, in particular of a body fluid. The system comprises three constituents, namely test carriers which contain in one or more test layers reagents whose reaction with the sample leads to a physically detectable change in a detection layer, code carriers which comprise in machine-readable form an evaluation code which is required for evaluating the physically detectable change and an evaluation device by which the physically detectable change is measured and converted into the analysis result.

Test carrier analysis systems are in common use particularly in medicine for the analysis of urine and blood. The test carriers are usually in the form of test strips. Other forms of test carriers are also used, however, for example flat, approximately square plates in the center of which a test field is situated.

The test layers are brought into contact with the sample, which in the case of the testing of urine generally takes place by immersion. In the case of the testing of blood, a drop of blood is usually dripped onto the test layer.

The physically detectable change is usually a colour change or another optically detectable property, for example fluorescence. Test carriers are also known, however, which are based on other, for example electrochemical principles, where the physically detectable change is related to an electric current or an electric voltage.

The evaluation device possesses a test carrier receiver for positioning in a measuring position a test carrier to be evaluated and a measuring device for measuring the physically detectable change. In the case of a colour change the measuring device contains a reflection photometer for determining the diffuse reflectivity of the detection layer. In the case of electrochemical test carriers the measuring device contains a corresponding current or voltage measurement circuit. In each case it determines a measurement signal R, from which the concentration C sought can be determined.

The test carriers are usually suited specifically to a particular analysis, i.e. one type of test carrier is used for determining the concentration of a particular constituent of a body fluid, said constituent being designated as a parameter. For a particular type of test carrier, for example for the analysis of glucose or cholesterol in blood, there is a particular relationship between the measurement signal R and the concentration C. Said relationship is designated as the evaluation curve.

A special problem has existed in this connection, however, since the very beginnings of quantitative analysis by means of test carriers. The test carriers are in fact produced in batches, and it is as a rule not possible to arrange the manufacturing process so as to be reproducible with such exactness that when high demands are made of the accuracy of the analysis, the same evaluation curve can be used for different manufacturing batches. A large number of suggestions for solving this problem have already been made.

A common method is calibration by means of calibration fluids of known concentration. It is usual in such systems to store in the evaluation instrument a mean evaluation curve which can be corrected from case to case on the basis of calibration measurements. This procedure is time-consuming and complicated, however, and therefore not very suitable particularly in analytical systems which are intended to be used by lay persons (so-called "home monitoring"), to which the invention relates to a particular degree.

In order to remedy this situation, analysis systems have been developed which incorporate, in addition to the test carriers and the evaluation device, special code carriers containing the evaluation information required for the evaluation. In one of the first systems for the analysis of glucose, a system which still worked on the analog electronic principle, use was made as code carriers for this purpose of replaceable graduated discs which were included in the respective test strip packs and whose graduation was coordinated with the respective batch-specific evaluation curve. Later the evaluation code was coded in machine-readable form. In many devices a read-only-memory (ROM) semiconductor module was used, which however contained not a batch-specific, but only a parameter-specific evaluation curve. In one particularly widely distributed system the code carrier consists of a film with a bar code which contains a batch-specific evaluation curve. The evaluation device comprises in such cases a code-reading device for reading the evaluation code and a storage means for storing the evaluation information coded in the evaluation code. The measurement signal is converted into the analysis result in accordance with this information.

The code carriers are in systems of this kind usually included in the test carrier packs. If a new pack of test carriers is opened, the user has in each case to load the code carrier into the evaluation instrument so that the evaluation information can be read and stored. This information can then be used as often as desired for the test carriers of the same pack. There is no certainty, however, that inadvertent use will not be made of a test carrier which does not belong to the batch whose evaluation curve has just been stored.

This problem may be solved by a positive batch identification, in which both the element used for the analysis and the code carrier exhibit a batch identification code which is read and compared in each case by the evaluation device. This arrangement is known, for example, from EP-A-0 353 589 for a system for testing for allergies. The embodiment described there, however, is suitable only for comparatively large laboratory systems.

There is also no risk of confusion with analysis systems in which the evaluation code is attached to the test carriers themselves and is read before each evaluation. In EP-A-73 056 and U.S. Pat. No. 4,592,893 a test strip is described which contains on its underside a bar code with a batch-specific evaluation curve. EP-A-132 790 (corresponding to U.S. Pat. No. 4,578,716) is concerned with the storage of the information in a magnetic layer situated on the test carriers. Such systems are almost completely secure against incorrect operation. This advantage is however offset by high expenditure in the manufacture of the test carriers, because it is necessary to apply to each batch a specific code of comparatively high information density under the difficult accompanying conditions typical of the manufacture of test strips. These problems are discussed in detail in the above-mentioned specifications.

The aim of the invention is to provide a test carrier analysis system which makes possible a precise analysis in accordance with the batch-specific evaluation curve without calibration by the user and in which incorrect operation is virtually eliminated without significantly increased manufacturing costs both as regards the test carriers and as regards the device.

The aim is achieved in the case of an analysis system operating with separate test carriers and code carriers by the combination of the following measures. The evaluation code on the code carriers is a two-track code with separate clock track and data track. There is provided on the test carriers a batch-specific identification code in the form of a bar code, the code bars of said identification code running over the whole width of the test carriers. The code reading device is arranged on the test carrier receiver so that both a test carrier and a code carrier can be inserted optionally and their codes read during the insertion and/or withdrawal. The code reading device comprises two reading units offset relative to one another both laterally and in the insertion direction. The evaluation device is equipped with a comparison unit which serves for comparing the identification code of the test carriers with the batch identification of the evaluation curve and hence for checking the correlation of the batch of the respective test carrier to be evaluated with the stored evaluation information.

The invention makes it possible for the evaluation code to be positively identified and hence for practically complete security to be provided against evaluation errors which could arise due to use of a wrong evaluation curve. This is achieved virtually without additional expenditure. A single code reading device can be used for reading the codes both on the test carriers and on the code carriers. Both codes are self-clocking and thus make possible even with manual movement of the code carriers and test carriers a high degree of reading reliability irrespective of the speed of movement of the code.

The two reading units offset laterally relative to one another are arranged so that one is directed towards the clock track and the other towards the data track of the evaluation code. The two-track code is particularly advantageous in conjunction with test carrier analysis systems, because it makes a very high information density possible and very small code carriers can therefore be used. This is necessary because increasingly smaller test carriers are being used, and if a single insertion path is used, the effective length of the code carriers is dependent on the corresponding length of the test carriers.

The fact that the code on the test carriers has to contain only the batch identification and is formed as a bar code with continuous code bars makes it possible to incorporate the application of the code into the normal test strip manufacturing process without significant additional expenditure. Because the reading units are offset relative to one another also in the direction of the insertion path (i.e. in the reading direction of the code), the identification code on the test strips can be read self-clocking, without a separate clock track being necessary or expensive measures having to be taken with respect to the device. This will be explained in greater detail below.

The bar code may be attached to the code carriers and the test carriers comparatively simply. Bar code reading devices are moreover simple and inexpensive. This is particularly important because the invention is particularly suitable for small, light, portable hand-sets such as are used in particular by diabetics.

For the reading of the code a guided relative movement between test carrier and code carrier is advantageous. The latter can be brought about in a suitable manner by providing the test carrier receiver with a guide which is constructed so that a test carrier can be inserted manually along an insertion path in the direction of the measuring position, the code reading device being arranged on said insertion path.

It is useful if the dimensions of the code carriers and the test carriers are coordinated with one another so that they can be packed together. For example, test strips are usually supplied in tubes and it is useful if the latter also contain a code carrier in strip form. This applies particularly to analysis systems which operate with different types of test carrier for determining different parameters and with which the correct code carriers for the respective parameter therefore have to be read prior to the evaluation. With such multi-parameter systems it would be vary awkward if the code carriers were to be packed separately from the test carriers.

In multi-parameter systems the identification code on the test carriers and the evaluation code on the code carriers contains in each case information on the type of test carrier (i.e. on the parameter), so that not only the correct correlation of the batch, but also the correct correlation of the type of test carrier with the respective evaluation curve can be checked or the respective evaluation curve required be retrieved from the storage means.

The invention will be described in detail below with reference to an embodiment represented diagrammatically in the figures, where FIG. 1 shows a perspective view of an analysis system according to the invention;

FIG. 2 a view of the coding side (underside) of a test carrier;

FIG. 3 a view of the coding side of a code carrier;

FIG. 4 a cross-section through the test carrier receiver region of an evaluation device in the insertion direction;

FIG. 5 a cross-section along the line V—V in FIG. 4 (at right angles to the insertion direction);

FIG. 6 a schematic diagram explaining the mode of operation of a code reading device.

FIG. 1 shows a test carrier analysis system 1, consisting of test carriers 2, code carriers 3 and an evaluation device 4.

The code carrier 2 and the test carrier 3 are designed in strip form. They have the same dimensions. Their carrying layer 2a or 3a is formed in each case from a rigid plastics sheet. The test carrier 2 comprises in the exemplifying case shown only a single test field 5 which may consist of a plurality of test layers.

The evaluation device 4 has an introduction opening 6 through which optionally a test carrier 2 or a code carrier 3 can be inserted into the test carrier receiver 7 situated inside the device and represented in dashes in the figure. A control panel 8 is provided for operating the device. The measurement results are indicated on a display 9.

As can be seen in FIG. 2, the test carrier 2 has on its underside a circular opening 10 through which the lowest layer 11 of the test field 5 can be distinguished. This is the detection layer, on which a colour change characteristic of the analysis takes place due to the reaction of the reagents contained in the test field 5 when a sample drop is applied to its top side. This colour change is measured by the evaluation device 4 and converted into the analysis result.

On the underside of the test carrier 2 there is further distinguished an identification code 12 and a bar-shaped mark 13 whose stripes each extend transversely across the whole test carrier.

As can be seen in FIG. 3, the code carrier 3 comprises on its coding side (which is the underside during the introduction into the evaluation device 4) an evaluation code 15 which consists of two tracks running parallel to one another, namely a clock track 16 and a data track 17.

In FIGS. 4 and 5 the front part of the evaluation device 4 is shown in two highly schematized cross-sectional drawings at right angles to one another. The test carrier receiver 7 includes a test carrier support 20, lateral guides 21a, 21b and two pressure springs 22, 23. By means of these elements both a test carrier 2 and a code carrier 3, which is introduced manually into the introduction opening 6, are guided along an insertion path 28 (FIG. 1). If a test carrier is located in the measuring position shown in FIG. 4, a catching element 24 preloaded in the direction of the test carrier support 20 engages with a catching projection 25 in a matching recess 26 in the test carrier 2. The recess 26 is located in the vicinity of the front end, i.e. in the introduction direction, of the test carriers 2. The catching projection 25 has a cross-section reducing in a downward direction. Its bottom end penetrates a depression 19 in the test carrier support 20. The catching projection 25 and the suspension of the catching element 24 are so formed and arranged that they press the test carrier 2 lightly against a stop 27 and thus position it exactly.

In the measuring position the test carrier 2 is pressed by the springs 22, 23 against the test carrier support 20. The pressure springs 22, 23 are constructed so that they yield elastically upwards on the insertion of the test carrier 2 without the hinged lid 30 having to be opened.

The positioning of the test carrier 2 in the measuring position as per FIG. 4 is very important for the accuracy of the evaluation. To enable it to be checked in a simple manner, the test carrier 2 comprises the mark 13 which in the measuring position is arranged opposite the code reading device 42.

The top covering of the test carrier receiver 7 is formed by a hinged lid 30, which is pivotable about hinges 31 (FIG. 1). During the introduction of the test carrier 2 the hinged lid 30 is in the closed position, the lateral guide 21 for the test carrier 2 being formed by the sides of a groove 32 constructed in the hinged lid 30. The hinged lid 30 capable of being swung open is required in particular on the following grounds.

Firstly, it is opened in order to apply to the test field 5 a drop of blood to be analyzed. The evaluation device 4 is in fact specifically constructed for so-called "non-wipeable" test carriers with which the application of the blood sample takes place onto the test carrier situated in the measuring position. This represents a considerable simplification of the handling compared with previously known test carrier analysis systems where the drop of blood has had to be dripped onto a test carrier situated outside the device, a certain waiting time then observed, and after this the excess blood wiped or washed off and finally the test carrier inserted into the device and evaluated. The invention is suitable to a particular degree for test carrier analysis systems which operate with non-wipeable test carriers.

Secondly, the test carrier 2 soiled after application of the blood sample may be removed upwards with the hinged lid 30 open, without soiling the components of the test carrier receiver 7. In order to prevent inadvertent removal of the test carrier 2 without opening of the hinged lid 30, the catching element 24 is supported movably in the direction of the introduction opening 6 (against a spring tension) and above it there is arranged on the hinged lid 30 a blocking element 33 by means of which the opening movement of the catching element (upwards) is blocked if one pulls on the test carrier 2 in the removal direction.

Thirdly, the test carrier support 20, which is held withdrawable by a catching lug 34 in a corresponding recess 35 in the bottom part 36, can be removed with the hinged lid 30 open and cleaned outside the device.

The test carrier 2 is so positioned in the measuring position that the measurement surface of the evaluation layer 11 is located exactly opposite a measurement window 37 provided in the test carrier support 20 and through which a reflection photometric measuring device 38 can measure the colour change of the evaluation layer 11. The measuring device 38 is conventionally constructed and can for example consist of a light emitting diode 39 as light transmitter and a photo transistor 40 as detector. A blank value measurement is preferably carried out on the dry detection layer 11 prior to the application of the sample.

On the insertion path 28 there is arranged between the lateral guides 21a, 21b and in the insertion direction in front of the measuring device 38 a code reading device 42, which includes two reading units 43 and 44 arranged offset laterally relative to one another. Miniaturized bar code readers of the usual type, merely indicated diagrammatically in the drawing, are involved here, which are based on the reflection principle and contain in each case a light transmitter and a light receiver.

A special feature consists in the fact that the code reading device 42 penetrates into a recess 20b in the test carrier support 20a in such a way that the upper sealing surface 45 of the code reading device is aligned approximately with the part which surrounds it of the surface 20a of the test carrier support 20, or projects slightly above said surface 20a. The block-shaped code reading device 42 is held by a holding part 42a in the casing of the evaluation device 4.

Between the test carrier receiver 20 and the bottom part 36 there runs a printed circuit board which incorporates the evaluation electronics. The electronic components can for example be located on the underside of the p.c. board 47, the bottom part 36 comprising a corresponding depression (not shown).

The evaluation electronics designated overall as 50 are represented in FIG. 5 simply in abstract form as a block. They incorporate measurement electronics 51, to which the measuring device 38 is connected and which generate from the output signal of the detector 40 a measurement signal, code reading electronics 52 for processing the signals of the reading units 43, 44 and a digital electronic unit 53 which contains a microprocessor. The digital electronic unit 53 comprises in particular a storage means 54 for storing items of information which have been read by the reading units 43, 44, together with a comparison unit 55.

The code reading device 42 serves for reading both the evaluation code 15 located on the code carriers 3 and the identification code 12 located on the test carriers 2. A code carrier 3 is preferably inserted up to the stop 27; it is not held firmly by the catching element 24 since it does not comprise a recess. The evaluation code 15 is read during the withdrawal. The reading of the identification code 12 takes place on the other hand each time a test carrier 2 is inserted. The code carrier 3 has to be inserted and read in each case before the first test carrier 2 of the respective batch is evaluated. The evaluation information coded in the evaluation code 15 contains the batch-specific evaluation curve of the test carrier batch and is stored in the storage means 54.

If a test carrier 2 is subsequently inserted, its identification code 12 is read and compared by means of the comparison circuit 55 with a batch identification which is likewise contained in the evaluation information stored in the storage means 54. If both batch identifications coincide, the measurement signal is converted into the analysis result by means of the stored evaluation curve. If on the other hand the batch of the inserted test carrier does not coincide with the batch of the stored evaluation curve, no evaluation takes place, instead an indication of the error is displayed on the display 9.

It is naturally also possible to load a plurality of different information items in succession if the storage means 54 is designed accordingly. This is particularly appropriate if the evaluation device 4 is to be used for the analysis of different parameters which are determined in random order. In this case the corresponding different types of code carrier are with advantage inserted in succession and the items of evaluation information coded in the evaluation codes 15 are stored. Whenever a test carrier 2 is inserted, its type and batch are recognized by means of the identification code 12 and a correlation with the stored evaluation curve of the corresponding parameter takes place, it being possible in turn also in this case for the correct batch information to be checked in the manner described above.

The invention thus makes simple handling of single-parameter or multi-parameter test carrier analysis systems possible, with virtually complete security against evaluation errors being achieved. The expenditure on equipment is on the other hand barely increased, because a single code reading device can be used both for reading the identification code on the test carriers and for reading the evaluation code on the code carriers.

The reading units 43, 44 of the code reading device 42 are offset relative to one another laterally (i.e. in the direction of the code bars) in such a way that they detect the clock track 16 and the data track 17 of the evaluation code 15 separately. A two-track code, such as is shown in FIG. 3, permits a high information density in a confined space and can at the same time be read independently of the insertion rate. This is important because preferably the code carriers 3, as well as the test carriers 2, are to be inserted into the evaluation device 4 manually without the assistance of electric power and because on the code carrier 3, which matches the test carriers 2 in size, only very little space is available for the application of the evaluation code 15. The test carriers and the code carriers preferably have a length of less then 7 cm, particularly preferably not more than 5 cm, and a width of less than 6 mm, preferably less than 5 mm. The width should come to less than 20% of the length.

The code carrier 3 length which can be used for the coding is smaller than the distance between the catching projection 25 and the code reading device 42. It comes to only about 2 cm in an embodiment of the invention tested under practical conditions. In comparison to a previously known device in which a comparatively long film strip was used as code carrier, some 60% of the information is accommodated on a quarter of the coding distance in this case. In the case of a two-track code of the kind shown in FIG. 3, each bar and each bar interval corresponds to one information unit (bit) whose content is determined by whether there is a code bar or not at the corresponding point on the data track. There are therefore virtually no intervals which are not used for the transmission of items of information.

The evaluation code 15 on the code carriers 3 can be applied comparatively cheaply and with high accuracy by screen printing.

With the test carriers 2 also, the same length is in principle available for the application of a code as with the code carriers. This length is however additionally shortened if—as in the case of the test carrier shown—the colour change on the evaluation layer 11 is evaluated on the same side (in the present case the underside) on which the code is also situated. In addition to this, the difficult conditions explained in detail in EP-A-73 056 (corresponding to U.S. Pat. No. 4,592,893) must be allowed for in the application of codes to test carriers. Test carriers in strip form are usually manufactured in the form of a long production ribbon whose width matches the length of the test carriers and onto which one or more test fields are applied continuously in the form of a narrow ribbon. Only at the end of the production process is the production ribbon divided up at right angles to its longitudinal direction into a large number of test strips. For the application of the bar code this means that the latter has to be printed continuously over the entire length of the initial ribbon (length for example 200 m). Moreover, the accuracy of the printing must be sufficiently good that it guarantees reliable reading of the code. Processes with which these conditions can be met are described in the named publications, but they are very expensive.

In the context of the present invention use is made as identification code 12 of a code whose code bars run over the whole width of the test carriers 2, so that the printing can be incorporated relatively simply and cheaply into the usual test carrier manufacturing process.

Although the identification code 12 is a simple single-track code, it is self-clocking in the sense that it can be read reliably independently of the insertion rate. This will be explained with reference to FIG. 6.

For the sake of clarity FIG. 6 shows the reading units 43 and 44 next to the identification code 12 inserted along the insertion path 28, whereas they are of course in reality arranged below the code. The reading units 43, 44 are offset relative to one another in the direction of the insertion path 28 (i.e. in the reading direction of the code). The identification code 12 possesses code bars of different width. The spacing of the reading units 43, 44 and the width and sequence of the code bars are coordinated with one another so that both reading units either see the same value ("black" or "white") or a different value. This corresponds to the bit values 0 and 1 and is independent of fluctuations in the insertion rate. In the position shown in FIG. 6, for example, the reading unit 44 "sees" a bar, 43 a bar interval. After a short displacement in the direction 28, 44 "sees" an interval and 43 a bar. On further displacement the center broad bar stands opposite both reading units, so that both see "black". A state in which both reading units see "white" is naturally also possible, but is not shown. To sum up, therefore, it is possible with such a coding method to represent reliably at will four different states independently of fluctuations in the insertion rate.

If the reading units 43, 44 of the code reading device 42 are offset relative to one another in the insertion direction as shown, this offsetting naturally has to be allowed for in the layout of the two-track code according to FIG. 3. This is however possible without any problem.

What is claimed is:

1. A test carrier analysis system comprising a test carrier, a code carrier, and an evaluation apparatus, for analyzing a constituent of a body fluid sample through the reaction of the body fluid with a reagent to produce a physically detectable change in a detection layer of the test carrier, where the change follows a particular relationship to a concentration of the constituent, in accordance with an evaluation curve which is dependent upon a particular manufacturing batch of a test carrier, said analysis being based on information supplied from the code carrier, and said physically detectable change being readable by the evaluation apparatus, said test carrier comprising reagents in at least one layer for reacting with the body fluid component to produce said physically detectable change in said detection layer, and a batch specific identification code in a form of a bar code with code bars running across a width of said test carrier;

said code carrier including an evaluation code on a surface thereof, said evaluation code containing an item of evaluation information including batch-specific information for forming a batch-specific evaluation curve, and wherein said evaluation code is a two-track bar code with separate clock track and data track, and said evaluation information contains a batch identification, said evaluation information being provided in a bar-code format;

said evaluation apparatus comprising test carrier receiver means for positioning said test carrier in a measuring position, measuring means for measuring said physically detectable change and for generating a measurement signal, said evaluation apparatus further comprising a) code reading means for reading said identification code of said test carrier and said evaluation code of said code carrier, said code reading means being arranged on said test carrier receiver means such that said test carrier or said code carrier can be inserted and their codes read by said code reading means, said code reading means comprising two reading units offset relative to each other laterally and longitudinally, with the longitudinal offset being in a direction of relative movement of said code carrier or said test carrier, said two reading units being laterally offset such that one of said units reads the clock track and another of said reading units reads the data track, and wherein said tracks of the evaluation code are offset in a longitudinal direction corresponding to the longitudinal offset of the reading units, and wherein a width and sequence of the code bars of the test carrier and the code carrier are coordinated with the longitudinal spacing of the reading units, whereby each of said test carrier and said code carrier are read individually by said code reading means, b) storage means for storing said evaluation information, and c) electronic evaluation means for converting said measurement signal in accordance with the stored items of information regarding said batch-specific evaluation curve, into an analysis result, wherein said evaluation apparatus also has comparison means for comparing the identification code of said test carrier with the batch identification of the evaluation curve, and for checking a correlation of the batch information of said test carrier to be evaluated with said evaluation information stored in said storing means.

2. A test carrier analysis system according to claim 1, wherein said test carriers and said code carriers are provided in a strip form.

3. A test carrier analysis system according to claim 1, wherein physical dimensions of said test carrier and said code carrier are coordinated in such a way that they can be packaged together.

4. A test carrier analysis system according to claim 2, wherein physical dimensions of said test carrier and said code carrier are coordinated in such a way that they can be packaged together.

5. A test carrier analysis system according to claim 1, wherein said test carrier further includes a mark for checking a correct positioning of said test carrier, said mark being arranged opposite to said code reading means when said test carrier is in said measuring position.

6. A test carrier analysis system according to claim 1, wherein said test carrier receiver means further comprises:

a removable test carrier support having a recess into which said code reading means penetrates when said test carrier support is in an inserted position, such that an upper surface of said code reading means and a surface of said test carrier support are approximately aligned.

7. A test carrier analysis system according to claim 1, further comprising a plurality of different types of test carriers containing different reagents for determining different sample constituents, and a plurality of code carrier types respectively correlated with the plurality of test carrier types, wherein the identification code on the test carriers and the evaluation code on the code carriers each contain information on the type of test carrier.

* * * * *

UNITED STATES PATENT AND TRADEMARK OFFICE
CERTIFICATE OF CORRECTION

PATENT NO. : 5,281,395
DATED : January 25, 1994
INVENTOR(S) : Ernst MARKART et al It is certified that error appears in the above-indentified patent and that said Letters Patent is hereby corrected as shown below:

On the cover page, Item [73], first line, change " Manheim " to -- Mannheim --.

On the cover page, Item [56], third reference, change " Rappender " to -- Ruppender --.

On the cover page, Item [56], tenth reference, change " Deitzer " to -- Dietze--.

Signed and Sealed this

Seventeenth Day of January, 1995

Attest:

BRUCE LEHMAN

Attesting Officer

Commissioner of Patents and Trademarks